(12) United States Patent
Quinn et al.

(10) Patent No.: US 7,807,453 B2
(45) Date of Patent: Oct. 5, 2010

(54) DEVICE FOR CELL CULTURE ON DEFORMABLE SURFACES

(75) Inventors: Thomas Quinn, Pierrefonds (CA); Hicham Majd, Renens (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 368 days.

(21) Appl. No.: 11/794,265

(22) PCT Filed: Jan. 4, 2006

(86) PCT No.: PCT/IB2006/050031

§ 371 (c)(1),
(2), (4) Date: Jun. 27, 2007

(87) PCT Pub. No.: WO2006/072911

PCT Pub. Date: Jul. 13, 2006

(65) Prior Publication Data

US 2008/0166796 A1  Jul. 10, 2008

(30) Foreign Application Priority Data

Jan. 7, 2005  (EP)  ................................. 05100076

(51) Int. Cl.
*C12N 5/00* (2006.01)
*C12N 5/02* (2006.01)
*C12M 1/00* (2006.01)
*C12M 3/00* (2006.01)

(52) U.S. Cl. ..................................... 435/289.1; 435/325
(58) Field of Classification Search .............. 435/289.1, 435/325
See application file for complete search history.

(56) References Cited

U.S. PATENT DOCUMENTS

| 4,839,280 | A | * | 6/1989 | Banes ...................... 435/305.2 |
| 5,324,636 | A | * | 6/1994 | Bartos et al. .................. 435/35 |
| 6,048,723 | A | * | 4/2000 | Banes ...................... 435/305.1 |
| 2004/0014205 | A1 | * | 1/2004 | Banes ........................ 435/325 |
| 2004/0058440 | A1 | | 3/2004 | Brown et al. |

FOREIGN PATENT DOCUMENTS

WO  WO 2004/090091 A2  10/2004

OTHER PUBLICATIONS

International Search Report mailed Apr. 4, 2006 in PCT/IB/2006/050031.
Written Opinion mailed Apr. 4, 2006 in PCT/IB/2006/050031.

* cited by examiner

*Primary Examiner*—Walter D Griffin
*Assistant Examiner*—Lydia Edwards
(74) *Attorney, Agent, or Firm*—Nixon & Vanderhye P.C.

(57) ABSTRACT

Device for the in vitro culture of cells comprising: a planar deformable substrate (3) with a culture surface (4), substrate deforming means for modifying the size of said culture surface (4), characterized by the fact that it furthermore comprises: substrate holding elements (5) which are located near the periphery of said culture surface (4), a frame (6,8) surrounding and directly or indirectly fixing said substrate holding elements (5), in such a way as to allow microscope viewing of the culture surface (4) and to avoid mechanical parts directly above or below the culture surface (4), said frame (6,8) being adapted to move said substrate holding elements (5) away from the center of said culture surface (4).

10 Claims, 6 Drawing Sheets

DEVICE FOR CELL CULTURE ON DEFORMABLE SURFACES

This application is the US national phase of international application PCT/IB2006/050031 filed 4 Jan. 2006 which designated the U.S. and claims benefit of EP 05100076.8, dated 7 Jan. 2005, the entire content of which is hereby incorporated by reference.

FIELD OF INVENTION

The invention relates to a device for the in vitro culture of cells on deformable substrates such as elastic membranes.

PRIOR ART

Different methods exist for culturing cells. Some cells grow best when they are able to attach themselves to a surface; such cells are referred to as adherent cells. Examples of adherent cells include skin, bone, and cartilage cells. Typically, adherent cells are cultured on rigid plastic surfaces; devices used for this purpose include petri dishes or T-flasks. Normally, adherent cells will multiply on these surfaces, increasing their population and occupying more and more of the surface. When the cells occupy essentially all of the available surface (confluence), they will often stop multiplying due to a phenomenon referred to as contact inhibition, and form a stable monolayer of cells. If further cell multiplication is desired, then the cell monolayer must be removed from the culture surface, the cells must be diluted, and then the cells must be placed back on a suitable surface where they can multiply again until they reach confluence. This process of removing cells from one surface, diluting them, and placing them on a new surface is referred to as passaging. Passaging often involves the use of enzymes to cut the links between cells and the culture surface, and between the cells themselves, in order to remove the cells from the culture surface and to dilute them. These enzymes destroy proteins at the cell surface, and may lead to loss of specialized cell functions. In general, passaging is associated with changes in cell behavior (Benya P D, Shaffer J D. Dedifferentiated chondrocytes reexpress the differentiated collagen phenotype when cultured in agarose gels. Cell 1982; 30:215-224) and the loss of specialized cell functions (Brodkin K R, Garcia A J, Levenston M E. Chondrocyte phenotypes on different extracellular matrix monolayers. Biomaterials 2004; 25(28):5929-38).

In order to avoid unnecessary passaging, it has been proposed to culture adherent cells on deformable surfaces (Frei H, Mueller W, Mainil-Varlet P, inventors; Method and device for the in vitro cultivation of cells patent application WO03020871. 2003). These surfaces must be able to deform by many times in order to compete with the increases in surface area which are possible by standard culture methods. For example, one passaging step where cells are transferred from one petri dish to three petri dishes involves an increase in the culture surface of 300%. Therefore, culture of adherent cells on a surface which is able to increase its available surface by many times is of significant practical interest because it may represent a way to multiply cells with less damage to them because fewer passaging steps are necessary. Culture of adherent cells on deformable surfaces is also of interest for other applications. In research studies of cell biomechanics, adherent cells are often allowed to attach to a surface, then the surface is deformed and the cell response to this mechanical stimulus is observed (Chiquet M, Renedo A S, Huber F, Fluck M. How do fibroblasts translate mechanical signals into changes in extracellular matrix production? Matrix Biol 2003; 22(1):73-80). Or similarly, cells are allowed to attach to a deformable surface and then the effects of the cell on the surface itself are observed as the cell performs some biological function (such as locomotion) (Pelham R J, Jr., Wang Y. High resolution detection of mechanical forces exerted by locomoting fibroblasts on the substrate. Mol Biol Cell 1999; 10(4):935-45) or cytoskeletal remodelling (Hinz B, Gabbiani G. Mechanisms of force generation and transmission by myofibroblasts. Curr Opin Biotechnol 2003; 14(5):538-46). Cells are known to respond biologically to mechanical stimuli, therefore devices and methods have been developed which involve culture of adherent cells on deformable surfaces in order to stimulate these cells by stretching. In general, cell biomechanics experiments or cell culture under mechanical stimulation by stretching involves changes in the area of the culture surface by about 10% (Winston F, Thibault L, Macarak E, inventors; Apparatus for mechanically stimulating cells U.S. Pat. No. 4,851,354. 1989; Shapiro A, Gray M, Melendez L, Schaffer J, Wright J, Venegas J, inventors; Cell stretching method U.S. Pat. No. 5,348,879. 1994; Laib J, Lee A, inventors; Biaxial strain system for cultured cells patent CA2305369. 2000; Banes A, inventor Loading station assembly and method for tissue engineering U.S. Pat. No. 6,472, 202. 2002; Sarem D, Sarem F, inventors; Cell and tissue culture device with controlled culture fluid flow U.S. Pat. No. 6,576,458. 2003), in order to avoid direct mechanical damaging of cells.

Culture of adherent cells on a deformable surface typically involves stretching a elastic membrane which serves as the culture surface. Several different types of devices have been reported or proposed for this application. For cell stimulation, a piston configuration is often used whereby an elastic membrane is attached at the edges and a solid surface is moved up against this surface from below in order to stretch it (or a vacuum is drawn to pull the membrane down over the piston. Alternatively, a chamber below the membrane may be filled with fluid in order to displace the membrane upwards or downwards and thereby stretch it. These approaches typically involve increases in membrane surface by about 10% and are not convenient for viewing cells with a microscope during membrane deformation because of the vertical movement of the membrane and because parts of the mechanism (notably the solid or fluid piston) are positioned along the optical axis where they limit the proximity to which a microscope objective may approach the cells. A hollow screw configuration has also been proposed which operates on a similar piston-like principle and addresses these limitations because the membrane surface remains flat and accessible to a microscope objective due to the avoidance of mechanical parts below the membrane. In cell biomechanics experiments, where microscopic observation of cells is of particular interest, devices have been described which operate using a mechanical principle similar to the hollow screw or hollow piston (Chiquet M, Renedo A S, Huber F, Fluck M. How do fibroblasts translate mechanical signals into changes in extracellular matrix production? Matrix Biol 2003; 22(1):73-80). These devices are also only capable of approximately 10% increases in culture surface area. Devices for the expansion of adherent cell populations by culture on a deformable surfaces have been proposed and described in several different configurations. An expanding membrane bubble configuration, an expanding sponge-like culture surface (RTMRecherches, inventor Device for three-dimensional cell culture, useful e.g. for producing tissue for transplantation, comprises flat, flexible pouch filled with porous textile material patent application FR2786783. 2000), and increased area for growth given by beads in spinner flask culture (Zeng M, Gianetti B, inventors;

Bioreactor with expandable surface area for culturing cells patent application WO2004020572. 2004) have been described. These configurations are inconvenient for microscopic viewing of cells because of vertical motion of the culture surface and because of device parts which limit the proximity to which a microscope objective may approach. A possible solution to these problems has been proposed with a transparent device to stretch a deformable membrane in a horizontal plane using an array of axes arranged in a radial configuration (UniBern. DC Bank Preis. UniLink 2003 Nov. 8, see also patent application WO 2004/090091). This design is limited by the presence of mechanical parts above or below the culture surface, which can inhibit viewing of cells or complicate the culture method due to increased risk of contamination. Also, this design is difficult to work with because it involves several different axes of control (one for each attachment point of the membrane).

OBJECTIVES OF THE INVENTION

To be useful in adherent cell culture for a wide range of applications including cell biomechanics experiments, mechanical stimulation of cells, and expansion of adherent cell populations with avoidance of unnecessary passaging, this invention achieves several goals including Must be lightweight and easy to manufacture from biocompatible materials Must be easy to sterilize Mechanical parts do not obstruct microscope viewing of the culture surface Mechanical parts have minimal risk of contaminating culture media Size and geometry compatible with standard incubators and microscopes Elastic membranes which serve as culture surfaces may be easily attached Can achieve enlargement of culture surface from about 1-1000%

Easily automated by monitoring and control of a single axis

SUMMARY OF THE INVENTION

The previous cited objectives are reached with the device according to the invention which comprises:
   a planar deformable substrate with a culture surface,
   substrate deforming means for modifying the size of said culture surface.

The device according to the invention is characterized by the fact that the substrate deforming means comprise:
   several substrate holding elements which are located near the periphery of the culture surface,
   a frame located around said substrate holding elements and fixing them directly or indirectly.

The substrate deforming means, optionally with the exception of the substrate holding elements, are not positioned above or below the culture surface.

In a preferred embodiment of the invention, the substrate holding elements are located above said culture surface. Alternatively, the substrate holding elements may be located below the culture surface or laterally, in the same plane as the one defined by the culture surface.

Advantageously, the culture surface has approximately a circular shape but any other shape, e.g. polygonal, can be used.

If a circular shape is used for the culture surface, the frame preferably has a ring shape.

In one preferred embodiment, the frame is made of an inner ring and an outer ring which are adapted to concentrically rotate with respect to each other. In this case, the substrate holding elements are directly or indirectly fixed to the rings in such a way that the rotation of one ring with respect to the other increases the size of the culture surface.

Advantageously, the substrate is designed to be easily attached or detached from the substrate holding elements. To this effect, the substrate may be bent around said substrate holding elements and secured to them with an elastic band.

The invention will be better understood with the examples below which are illustrated by the following figures:

FIG. 1a shows an horizontal cross section of the elastic substrate and the substrate holding elements.

FIG. 1b shows a side cross section of the device of FIG. 1a.

FIG. 1c shows an horizontal cross section of the elastic substrate and the substrate holding elements, for a more highly adapted design of the connections between the two.

FIG. 1d shows a side cross section of the device of FIG. 1c.

Figure 4:
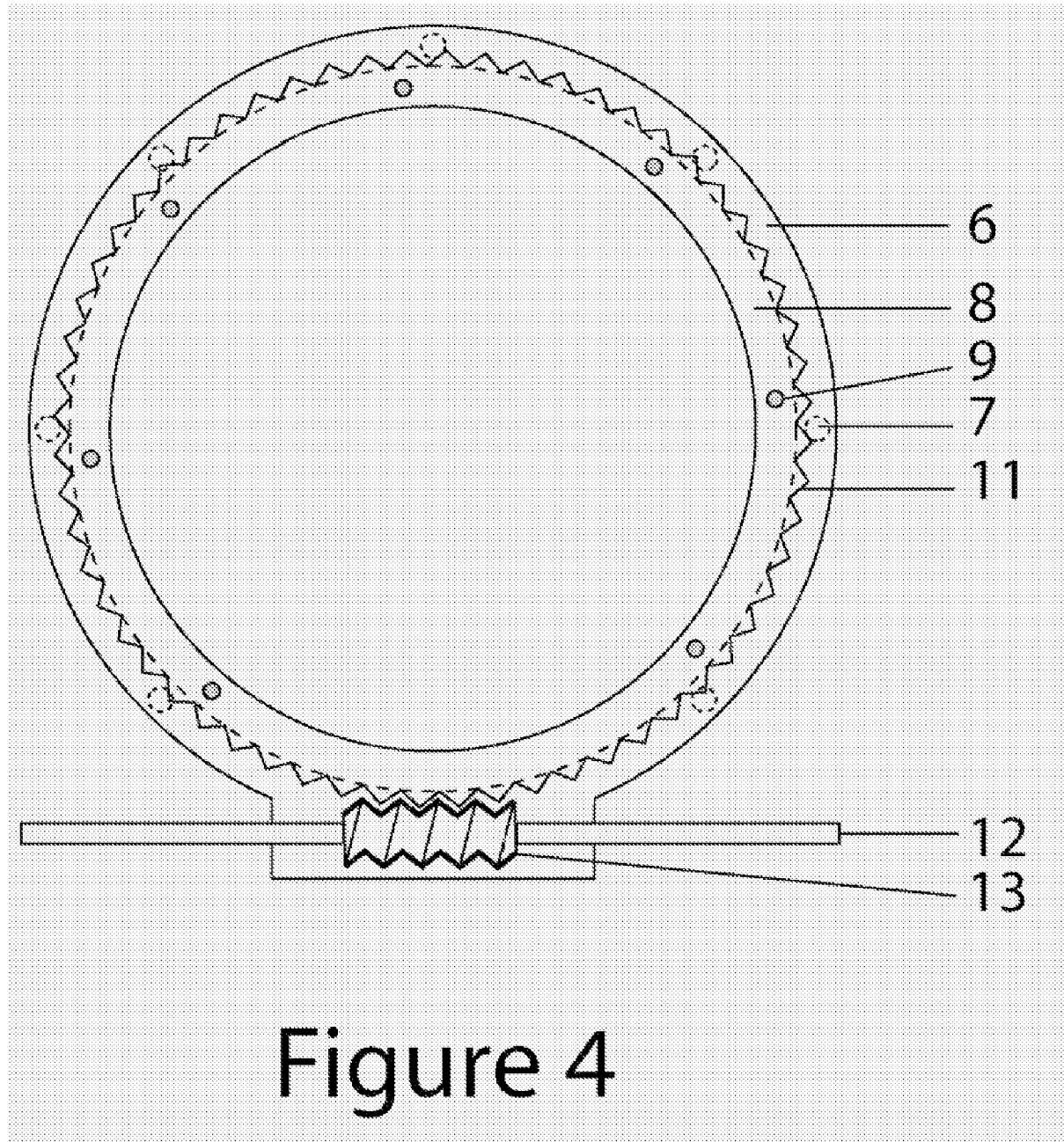

FIG. 4 schematically shows a frame driving means.

Figure 5:
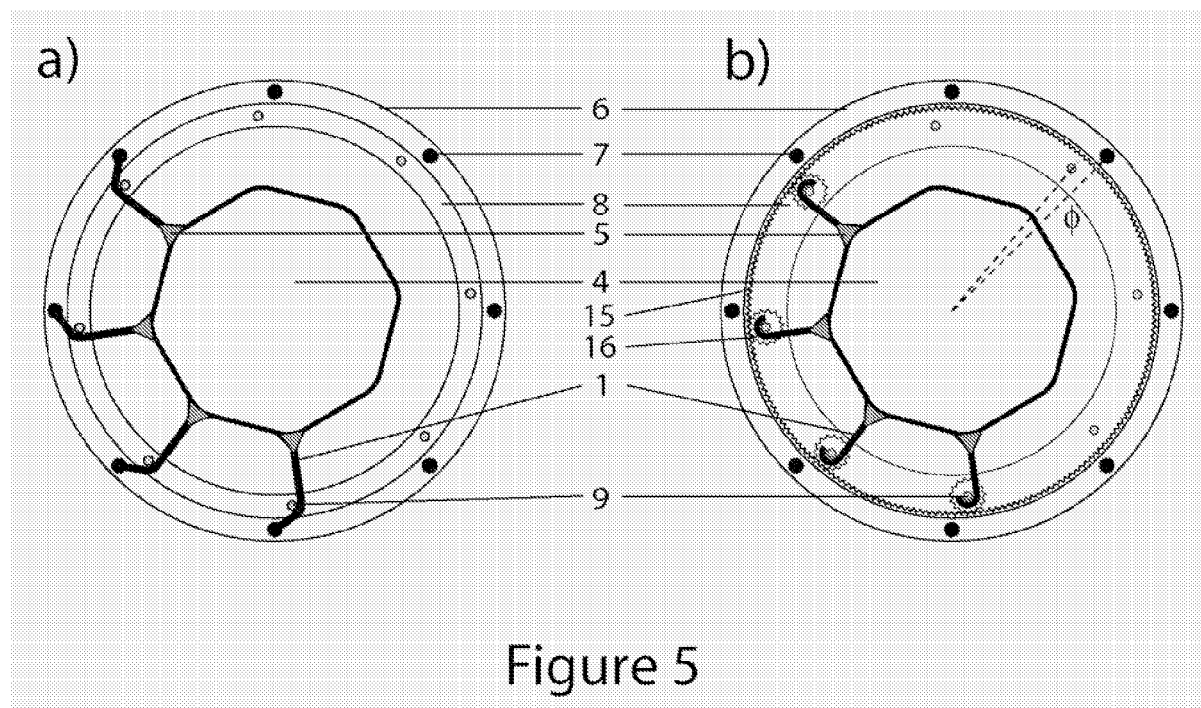

FIG. 5 shows an upper view of two other possible embodiments of the device while the culture surface is changing.

Figure 6:
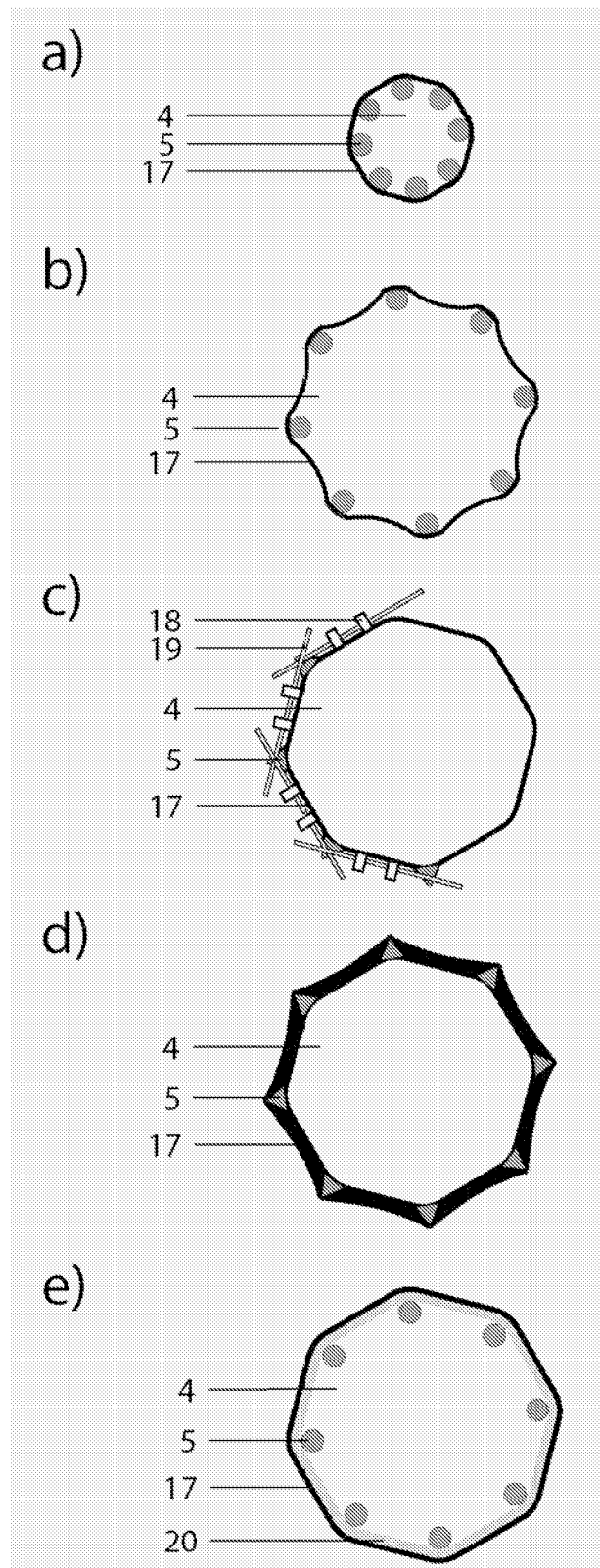

FIG. 6a shows an upper view of the elastic substrate before the culture surface is increased.

FIGS. 6b-e show upper views of the elastic substrate after the culture surface has been increased, with different approaches having been taken to influence the way in which the culture surface deforms.

Figure 1:
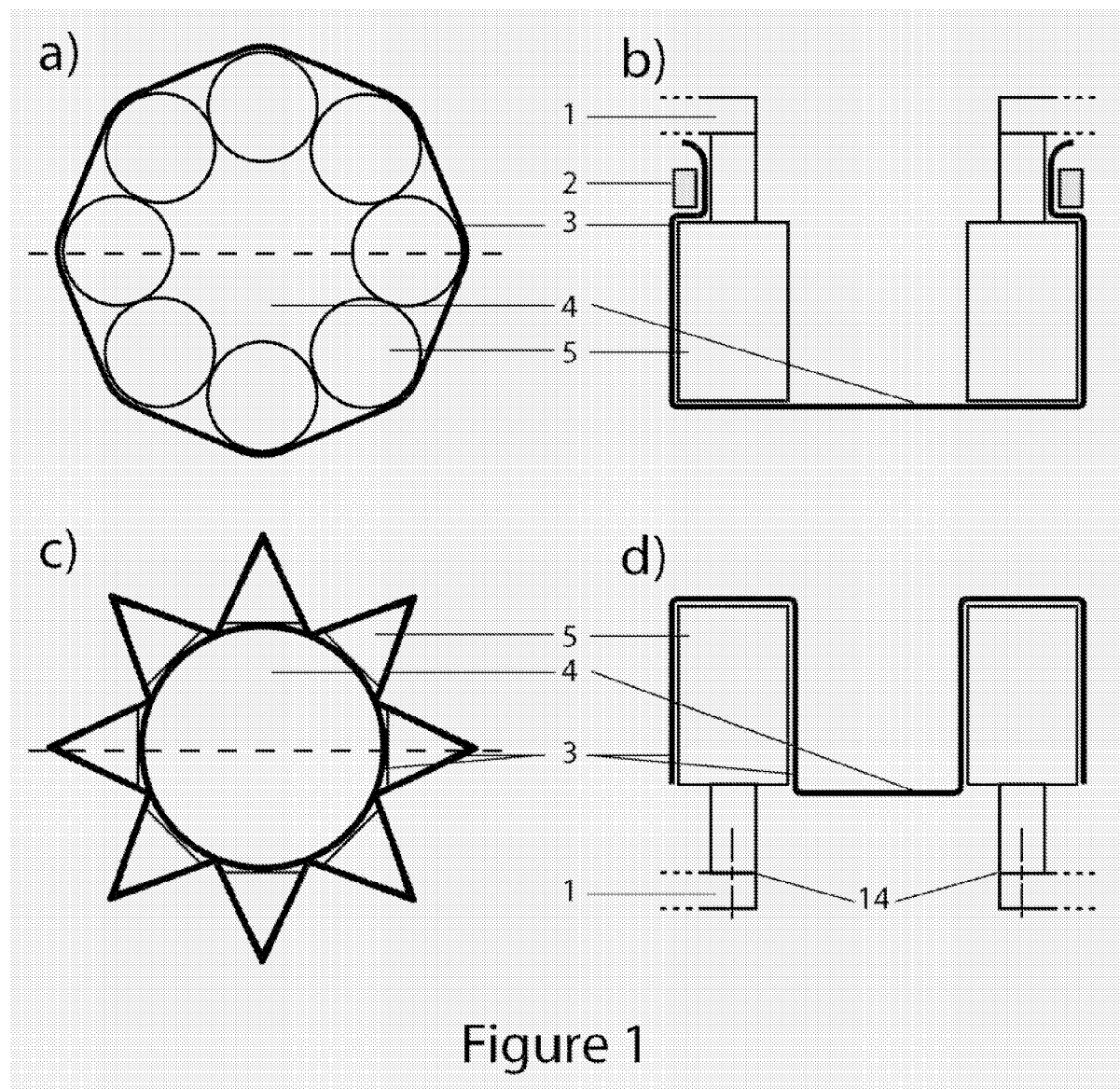

At the heart of the device (FIG. 1) lies a deformable culture surface 4, such as an elastic membrane 3, upon which adherent cells are cultured. This membrane 3 is attached to a series of posts 5 which then determine the shape of the horizontal culture surface 4. The attachment may be performed simply by bending the membrane 3 around the posts 5 and securing it with an elastic band 2 (FIG. 1b) or, for example, by manufacturing the membranes and/or the posts such that the membrane 3 fits to the posts 5 in a more adapted fashion. For example, the membrane 3 could be manufactured such that it includes walls extending perpendicularly away from the culture surface 4, with spaces inside these walls for the posts 5 (FIG. 1d). The attachment posts 5 are connected to arms 1 which extend away from the culture surface 4. It may be advantageous to make the connections between the posts 5 and the arms 1 rigid, or as a pivot 14 which is free to rotate.

Figure 2:
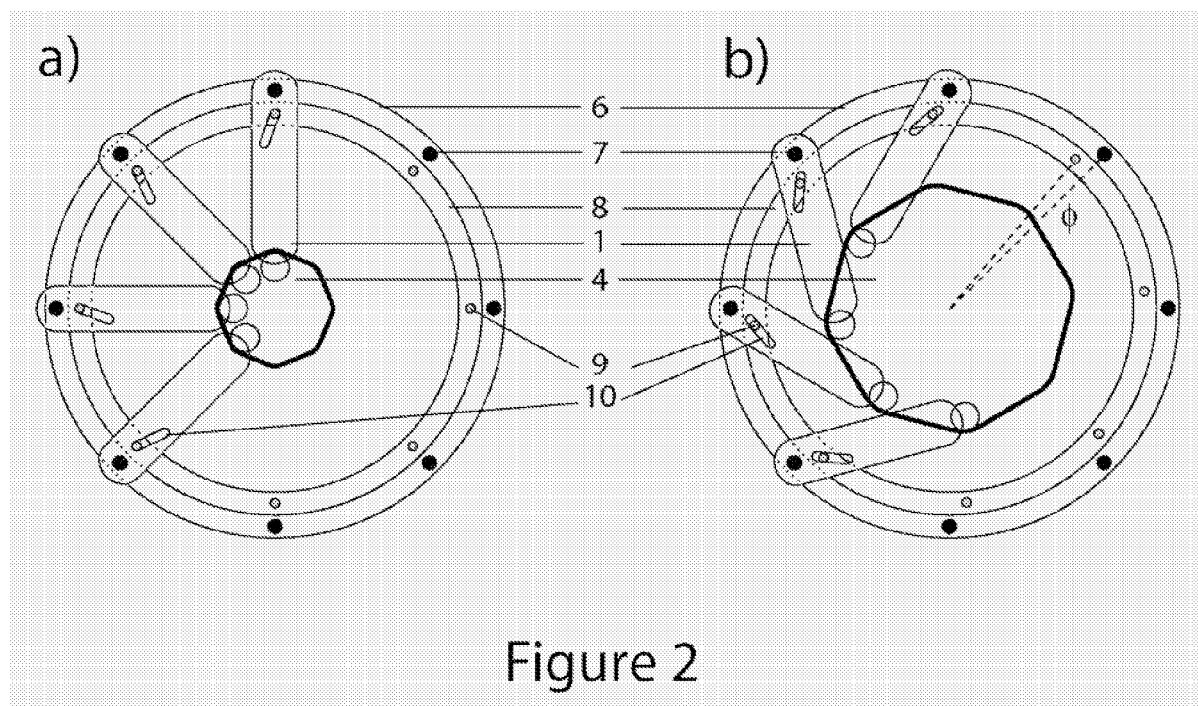
FIG. 2a shows an upper view of the device before the culture surface is increased.
FIG. 2b shows an upper view of the device after having increased the culture surface.
Figure 3:
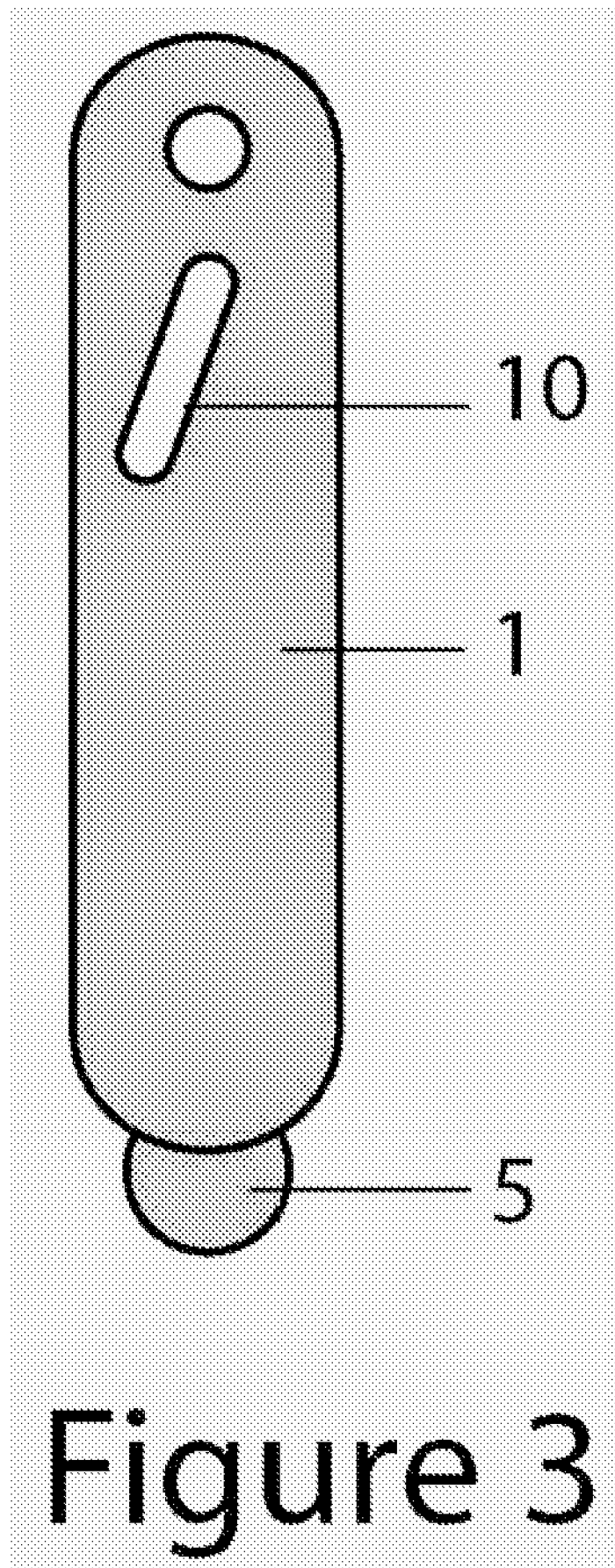
FIG. 3 represents a detailed view of an arm.

The arms 1 are attached to pivot points 7 which are fixed in an outer ring 6 near the outer boundary of the device (FIG. 2a). Therefore, when the arms 1 rotate about these pivot points 7, the positions of the membrane attachment points 5 will change. Inside the outer ring 6 an inner ring 8 is positioned which is able to rotate concentrically with the outer ring 6. The inner ring 8 carries a series of guideposts 9, each of which is fixed in the inner ring 8 and is able to slide within a slot 10 carved into one of the arms 1 (for details of the arms 1, see FIG. 3). As the inner ring 8 rotates with respect to the outer ring 6, see angle φ on FIG. 2b, the guideposts 9 and slots 10 will cause the arms 1 to turn and the surface area 4 of the elastic membrane 3 to change (FIG. 2).

The final size of the membrane 3 approximately determined by the size of the inner ring 8, which may be as big as desired. The initial size of the membrane 3 is determined by the size of the outer ring 6 and the length of the arms 1, and may be as small as desired. Therefore, there is essentially no limitation to the factor of increase in surface area which is possible with this mechanism.

The arms 1 always remain oriented such that they extend away from the culture surface 4. The inner 8 and outer 6 rings are always larger than the culture surface 4. No mechanical parts (except the attachment posts 5 but this can be overcome by adaptation of the membrane 3 and post 5 geometry) are ever positioned above or below the culture surface 4. Therefore, the risk of culture contamination due to mechanical parts above the culture media is minimal.

Also, the elastic membrane culture surface 4 always remains unobstructed for viewing with a microscope, particularly with an inverted microscope (from below).

Furthermore, the access to said culture surface, e.g. hand of a user or instrument, is facilitated.

The slots 10 carved in the arms 1 determine the relationship between the angle of rotation between the inner and outer rings φ and the membrane surface area 4. Therefore, the shape of these slots 10 may be adapted for specific purposes. For example, for linear or exponential relationships between the angle of rotation φ and the surface 4, or for another example, the arms 1 could be made to turn individually by different amounts (due to different slot-shapes in each arm 1) so that stretching of the membrane 3 is not the same in all directions.

Rotation of the inner ring 8 within the outer ring 6 could be supplied, for example (FIG. 4), by a gear 11 fixed on the inner ring 8 articulating with a worm screw 13 rotating on an axis 12 fixed in the outer ring 6. Other configurations are possible but this method has the advantages of being mechanically efficient (good mechanical advantage) and also preventing relative rotation of the rings 6,8 once a desired position has been achieved.

The membrane surface area 4 may therefore be changed with the rotation of a single axis, which is a significant advantage for motorization. Furthermore, a one-to-one correspondence can exist between the position of this axis, the relative angle between the two rings 6,8, the angle of rotation of the arms, and the membrane surface area 4. Therefore, monitoring of any one of these angles could provide a means for automated monitoring of the membrane surface area 4.

In other possible embodiments of the device, the arms 1 may consist of deformable cords or straps (FIG. 5). The arms 1 may be attached at the pivot points 7 and then pass around the guideposts 9 and then attach to the holding elements 5. The rings 6,8 rotate relative to one another with the result that the arms 1 cause the holding elements 5 to move radially in order to change the size of the culture surface 4 as illustrated in FIG. 5a. The arms 1 may also be attached to a small wheel gear 16 which rotates around the guidepost 9 and as the wheel gear 16 rotates, the arms 1 are wound around the guidepost 9. Therefore, when the rings 6,8 rotate relative to one another, the wheel gears 16 turn due to their interaction with the surrounding gear 15 mounted in the outer ring 6 with the result that the arms 1 cause the holding elements 5 to move radially in order to change the size of the culture surface 4 as illustrated in FIG. 5b.

Different approaches may also be taken in order to influence the way that the culture surface 4 deforms while the holding elements 5 move. Stretching of the culture surface 1 may tend to cause inward bending of the walls 17 of the elastic membrane 3 (FIGS. 6a,b). This would tend to cause non-uniform stretching of the culture surface 4 which may be undesirable. Embodiments of the device may be introduced which compensate for this and promote uniform stretching of the culture surface 4. Rigid bars 19 may be introduced into holes in the holding elements 5 and attachment clips 18 may be used to fix the walls 17 of the elastic membrane 3 to the rigid bars 19 (FIG. 6c). If the rigid bars 19 can slide through the holes in the holding elements 5, and if the attachment clips 18 can slide along the rigid bars 19, then the inward bending of the walls 17 of the elastic membrane 3 can be reduced. Also, the walls 17 of the elastic membrane 3 may be made less easily deformable than the culture surface 4 (for example by increasing their thickness or changing their composition), so that the inward bending of the walls 17 of the elastic membrane 3 is reduced (FIG. 6d). Also, between the holding elements 5 and the walls 17 of the elastic membrane 3, an elastic support band 20 may be introduced which resists the inward bending of the walls 17 of the elastic membrane 3 (FIG. 6e).

The invention claimed is:

1. A device for the in vitro culture of cells comprising:
   a planar deformable substrate with a culture surface,
   substrate deforming means that results in planar deformation of the substrate for modifying the size of said culture surface and,
   wherein said substrate deforming means comprise:
   several substrate holding elements which are located near the periphery of said culture surface,
   a frame located around said substrate holding elements and fixing them directly or indirectly,
   said substrate deforming means, optionally with the exception of said substrate holding elements, being not positioned above or below said culture surface.

2. The device according to claim 1 wherein said substrate holding elements are located above, below, or to the side of said culture surface.

3. The device according to claim 1 wherein said culture surface has substantially a circular shape and said frame has a ring shape.

4. The device according to claim 3 wherein said frame is made of an inner ring and an outer ring adapted to concentrically rotate with respect to each other, said substrate holding elements being directly or indirectly fixed to said rings.

5. The device according to claim 1 wherein said substrate is designed to be easily attached or detached from the substrate holding elements.

6. The device according to claim 5 wherein said substrate is bent around said substrate holding elements and secured to them with an elastic band.

7. The device according to claim 5 wherein said substrate contains spaces within walls extending away from the culture surface for insertion of holding elements.

8. The device according to claim 1 wherein said culture surface has a shape which changes during expansion or contraction due to different movements of the substrate holding elements.

9. The device according to claim 1 wherein said holding elements may be rigidly fixed to arms, or rotation is allowed between said holding elements and said arms.

10. The device according to claim 1 further comprising means for promoting uniform deformation of said culture surface.

* * * * *